US008101155B2

(12) United States Patent
Torok-Storb

(10) Patent No.: US 8,101,155 B2
(45) Date of Patent: Jan. 24, 2012

(54) SEQUENCE OF STRO-1 ANTIBODY VARIABLE REGION

(75) Inventor: Beverly Torok-Storb, Seattle, WA (US)

(73) Assignee: Fred Hutchinson Cancer Research Center, Seattle, WA (US)

(*) Notice: Subject to any disclaimer, the term of this patent is extended or adjusted under 35 U.S.C. 154(b) by 627 days.

(21) Appl. No.: 12/160,248

(22) PCT Filed: Jan. 16, 2007

(86) PCT No.: PCT/US2007/001046
§ 371 (c)(1),
(2), (4) Date: Aug. 11, 2008

(87) PCT Pub. No.: WO2007/089419
PCT Pub. Date: Aug. 9, 2007

(65) Prior Publication Data
US 2009/0068096 A1 Mar. 12, 2009

Related U.S. Application Data

(60) Provisional application No. 60/763,235, filed on Jan. 30, 2006.

(51) Int. Cl.
*A61K 51/00* (2006.01)
*A61M 36/14* (2006.01)
(52) U.S. Cl. ............... 424/1.49; 424/1.11; 424/1.65; 424/1.69; 424/9.1; 424/9.2; 530/300; 530/324; 514/1; 514/1.1
(58) Field of Classification Search ............. 424/1.11, 424/1.49, 1.65, 1.69, 1.73, 9.1, 9.2; 436/512, 436/513, 547, 548; 530/300, 324; 514/1, 514/1.1
See application file for complete search history.

(56) References Cited

U.S. PATENT DOCUMENTS

| 6,914,129 B2 | 7/2005 | Jardieu et al. | |
| 6,924,360 B2 | 8/2005 | Green et al. | |
| 6,949,244 B1 | 9/2005 | Chatterjee et al. | |
| 2005/0152899 A1* | 7/2005 | Kinch et al. | 424/144.1 |

FOREIGN PATENT DOCUMENTS

| WO | WO 01/04268 A1 | 1/2001 |
| WO | WO 03/016916 A1 | 2/2003 |

OTHER PUBLICATIONS

R&D Systems Ordering Information. Monoclonal Anti-human STRO-1 Antibody. R&D Systems, Inc. Jul. 21, 2005, 1 page.
International Search Report and Written Opinion, PCT/US07/01046, mailed Jul. 11, 2008.
Shi S and Gronthos S. Perivascular niche of postnatal mesenchymal stem cells in human bone marrow and dental pulp. Journal of Bone and Mineral Research. 2003; 18(4): 696-704.
Abdallah BM and Kassem M. Human mesenchymal stem cells: from basic biology to clinical applications. Gene Therapy. 2008; 15: 109-116.
Simmons PJ and Torok-Storb B. Identification of stromal cell precursors in human bone marrow by a novel monoclonal antibody, STRO-1. Blood. Jul. 1, 1991; 78(1): 55-62.
Simmons PJ and Torok-Storb B. CD34 expression by stromal precursors in normal human adult bone marrow. Blood. Dec. 1, 1991; 78(11): 2848-2853.
Gronthos S et al. The STRO-1+ fraction of adult human bone marrow contains the osteogenic precursors. Blood. Dec. 15, 1994; 84(12): 4164-4173.
Simmons PJ et al. Isolation, characterization and functional activity of human marrow stromal progenitors in hemopoiesis. Advances in Bone Marrow Purging and Processing: Fourth International Symposium. 1994: 271-280.
Oyajobi BO et al. Isolation and characterization of human clonogenic osteoblast progenitors immunoselected from fetal bone marrow stroma using STRO-1 monoclonal antibody. Journal of Bone and Mineral Research. 1999; 14(3): 351-361.
Davies J and Riechmann L. Affinity improvement of single antibody VH domains: residues in all three hypervariable regions affect antigen binding. Immunotechnology. 1996; 2: 169-179.
Stewart K et al. Further characterization of cells expressing STRO-1 in cultures of adult human bone marrow stromal cells. Journal of Bone and Mineral Research. 1999; 14(8): 1345-1356.
Holt LJ et al. Domain antibodies: proteins for therapy. Trends in Biotechnology. Nov. 2003; 21(11): 484-490.
Stewart K et al. STRO-1, HOP-26 (CD63), CD49a and SB-10 (CD166) as markers of primitive human marrow stromal cells and their more differentiated progeny: a comparative investigation in vitro. Cell Tissue Res. 2003; 313: 281-290.
Supplementary European Search Report, EP 07762880, mailed May 6, 2010.

* cited by examiner

*Primary Examiner* — D L Jones
(74) *Attorney, Agent, or Firm* — Myers Bigel Sibley & Sajovec, P.A.

(57) ABSTRACT

The amino acid sequence of the heavy chain polypeptide and the light chain polypeptide of the STRO-1 antibody is disclosed. Also disclosed are methods for detecting and isolating cells expressing the STRO-1 cell surface protein.

11 Claims, No Drawings

SEQUENCE LISTING

<160> NUMBER OF SEQ ID NOS: 8

<210> SEQ ID NO 1
<211> LENGTH: 114
<212> TYPE: PRT
<213> ORGANISM: Artificial
<220> FEATURE:
<223> OTHER INFORMATION: Recombinant antibody heavy chain polypeptide
      sequence

<400> SEQUENCE: 1

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
                20                  25                  30

Tyr Met His Trp Val Lys Gln Ser His Gly Lys Ser Leu Glu Trp Ile
            35                  40                  45

Gly Arg Val Asn Pro Asn Asn Gly Gly Thr Ser Tyr Asn Gln Lys Phe
    50                  55                  60

Lys Gly Lys Ala Ile Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Thr Tyr Ala Met Asp Tyr Trp Gly Gln Gly Thr Ser Val Thr Val
            100                 105                 110

Ser Ser

<210> SEQ ID NO 2
<211> LENGTH: 120
<212> TYPE: PRT
<213> ORGANISM: Artificial
<220> FEATURE:
<223> OTHER INFORMATION: Recombinant antibody light chain sequence

<400> SEQUENCE: 2

Trp Asn Asp Val Leu Cys Ser Leu Val Asp Leu Cys Arg Ala Cys Ser
1               5                   10                  15

Ser Gln Ala Ser Val Ser Thr Gln Thr Asp Tyr Leu Thr Thr Ser Pro
                20                  25                  30

Gly Gly Thr Val Ile Leu Thr Cys Arg Cys Ala Thr Gly Ala Val Thr

```
                35                  40                  45
Thr Ser Asn Tyr Ala Asn Trp Val Gln Glu Lys Pro Asp His Leu Phe
 50                  55                  60

Thr Gly Leu Ile Gly Gly Thr Ser Asn Arg Ala Pro Gly Val Pro Val
 65                  70                  75                  80

Arg Phe Ser Gly Ser Leu Ile Gly Asp Lys Ala Ala Leu Thr Ile Thr
                 85                  90                  95

Gly Ala Gln Thr Glu Asp Asp Ala Met Tyr Phe Ser Ser Leu Trp Tyr
            100                 105                 110

Tyr Gly Gly His Gly Val Phe Gly
        115                 120

<210> SEQ ID NO 3
<211> LENGTH: 5
<212> TYPE: PRT
<213> ORGANISM: Artificial
<220> FEATURE:
<223> OTHER INFORMATION: Recombinant antibody heavy chain hypervariable
      region sequence

<400> SEQUENCE: 3

Gly Tyr Tyr Met His
1               5

<210> SEQ ID NO 4
<211> LENGTH: 16
<212> TYPE: PRT
<213> ORGANISM: Artificial
<220> FEATURE:
<223> OTHER INFORMATION: Recombinant antibody heavy chain hypervariable
      region sequence

<400> SEQUENCE: 4

Arg Val Asn Pro Asn Asn Gly Gly Thr Ser Tyr Asn Gln Lys Phe Lys
1               5                   10                  15

<210> SEQ ID NO 5
<211> LENGTH: 8
<212> TYPE: PRT
<213> ORGANISM: Artificial
<220> FEATURE:
<223> OTHER INFORMATION: Recombinant antibody heavy chain hypervariable
      region sequence

<400> SEQUENCE: 5

Tyr Cys Ala Thr Tyr Ala Met Asp
1               5

<210> SEQ ID NO 6
<211> LENGTH: 11
<212> TYPE: PRT
<213> ORGANISM: Artificial
<220> FEATURE:
<223> OTHER INFORMATION: Recombinant antibody light chain hypervariable
      region sequence

<400> SEQUENCE: 6

Gln Thr Asp Tyr Leu Thr Thr Ser Pro Gly Gly
1               5                   10

<210> SEQ ID NO 7
<211> LENGTH: 7
<212> TYPE: PRT
<213> ORGANISM: Artificial
<220> FEATURE:
<223> OTHER INFORMATION: Recombinant antibody light chain hypervariable
```

-continued

```
region sequence

<400> SEQUENCE: 7

Ser Asn Tyr Ala Asn Trp Val
1               5

<210> SEQ ID NO 8
<211> LENGTH: 9
<212> TYPE: PRT
<213> ORGANISM: Artificial
<220> FEATURE:
<223> OTHER INFORMATION: Recombinant antibody light chain hypervariable
      region sequence

<400> SEQUENCE: 8

Asp Lys Ala Ala Leu Thr Ile Thr Gly
1               5
```

SEQUENCE OF STRO-1 ANTIBODY VARIABLE REGION

RELATED APPLICATIONS

This application is a national phase application of PCT Application PCT/US2007/001046, filed Jan. 16, 2007, and published in English on Aug. 9, 2007, as International Publication No. WO 2007/089419, and which claims the benefit of U.S. Provisional Patent Application Ser. No. 60/763,235, filed Jan. 30, 2006, the disclosure of each of which is incorporated by reference herein in its entirety.

FIELD OF THE INVENTION

This invention relates to derivatives of STRO-1 monoclonal antibodies and methods of use thereof.

BACKGROUND OF THE INVENTION

The STRO-1 antibody was obtained from a hybridoma produced from B cells obtained from a mouse immunized with a human $CD34^+$ bone marrow cells (P. Simmons and B. Torok-Storb, *Blood* 78, 55-62 (1991)).

STRO-1 is a cell surface protein expressed by bone marrow stromal cells and erythroid precursors. Marrow cells that express STRO-1 antigen are capable of differentiating into multiple mesechymal lineages, including hematopoiesis-supportive stromal cells, adipocytes, osteoblasts, and chondrocytes.

Mouse monoclonal anti-human STRO-1 antibody is commercially available from R&D Systems, Inc. (Minneapolis, Minn., USA) under catalog number MAB 1038.

Additional discussion of uses for Stro-1 antibodies is given in U.S. Pat. Nos. 7,122,178; 7,057,738; and 5,677,136; and in US Patent Application Publication Nos. 20060286077; 20060182724; 20060088890; and 20060057720.

SUMMARY OF THE INVENTION

The present invention concerns STRO-1 antibodies and their use in detection of cells comprising the STRO-1 cell surface protein and in the preparation of a substantially purified population of cells comprising the STRO-1 cell surface protein.

In one aspect, the invention concerns a recombinant antibody comprising a heavy chain polypeptide, wherein the polypeptide has an amino acid sequence of SEQ ID NO:1, or hypervariable region thereof, and further wherein the antibody binds to human STRO-1 cell surface protein.

A further embodiment of the present invention comprises a recombinant antibody comprising a heavy chain polypeptide further comprising a hypervariable region of SEQ ID NO:1, wherein the hypervariable region is selected from the group of sequences comprising SEQ ID NO:3, SEQ ID NO:4 and SEQ ID NO:5, or any combination thereof.

Another aspect of the present invention provides a recombinant antibody comprising a heavy chain polypeptide and a light chain polypeptide, wherein the heavy chain polypeptide has an amino acid sequence of SEQ ID NO:1, or hypervariable region thereof, and the light chain polypeptide has an amino acid sequence of SEQ ID NO:2, or hypervariable region thereof, and further wherein the antibody binds to human STRO-1 cell surface protein.

Another embodiment of the present invention comprises a recombinant antibody comprising a light chain polypeptide further comprising a hypervariable region of SEQ ID NO:2, wherein the hypervariable region is selected from the group of sequences comprising SEQ ID NO:6, SEQ ID NO:7 and SEQ ID NO:8, or any combination thereof.

An additional embodiment of the present invention provides a method of isolating a cell in a cell sample, wherein the cell binds an antibody to human STRO-1 cell surface protein, the method comprising contacting a cell sample with an antibody of the present invention under conditions whereby the antibody can bind the STRO-1 cell surface protein of the cell, and isolating the cell in the cell sample that binds to the antibody from the cells in the sample that do not bind to the antibody.

Another embodiment of the present invention provides a method of detecting a cell in a cell sample, wherein the cell comprises the human STRO-1 cell surface protein, the method comprising contacting the cell sample with an antibody of the present invention under conditions whereby the antibody can bind the STRO-1 cell surface protein of the cell, and detecting the binding of the antibody to the cell in the sample thereby detecting the cell comprising the human STRO-1 cell surface protein in the sample.

Another aspect of the invention is an antibody as described herein conjugated to a therapeutic agent.

Still another aspect of the invention is a method of inactivating a Stro-1 positive stem cell, comprising contacting a Stro-1 positive stem cell (in vitro or in vivo) to an antibody as described herein (particularly one having a therapeutic agent conjugated thereto), with the antibody provided in an amount effective to inactivate said Stro-1 positive stem cell.

Still another aspect of the invention is the use of an antibody as described herein for the preparation of a medicament for carrying out a method as described herein.

DETAILED DESCRIPTION OF THE PREFERRED EMBODIMENTS

The present invention is explained in greater detail below. This description is not intended to be a detailed catalog of all the different ways in which the invention may be implemented, or all the features that may be added to the instant invention.

For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof. The disclosure of all U.S. patent references cited herein are intended to be incorporated herein by reference in their entirety.

Table of Sequences Disclosed Herein

| SEQ ID NO:1 | EVQLQQSGPD | LVKPGASVKI | SCKASGYSFT |
|---|---|---|---|
| | GYYMHWVKQS | HGKSLEWIGR | VNPNNGGTSY |
| | NQKFKGKAIL | TVDKSSSTAY | MELRSLTSED |
| | SAVYYCATYA | MDYWGQGTSV | TVSS |
| SEQ ID NO:2 | WNDVLCSLVD | LCRACSSQAS | VSTQTDYLTT |
| | SPGGTVILTC | RCATGAVTTS | NYANWVQEKP |
| | DHLFTGLIGG | TSNRAPGVPV | RFSGSLIGDK |
| | AALTITGAQT | EDDAMYFSSL | WYYGGHGVFG |

-continued

Table of Sequences Disclosed Herein

SEQ ID NO:3  GYYMH

SEQ ID NO:4  RVNPNNGGTSYNQKFK

SEQ ID NO:5  YCATYAMD

SEQ ID NO:6  QTDYLTTSPGG

SEQ ID NO:7  SNYANWV

SEQ ID NO:8  DKAALTITG

"Therapeutic group" as used herein may be any group capable of killing, or limiting the replication of, a cell to which the therapeutic group is administered, including but not limited to radionuclides, chemotherapeutic agents, and cytotoxic agents.

"Radionuclide" as described herein may be any radionuclide suitable for delivering a therapeutic dosage of radiation to a tumor or cancer cell, including but not limited to $^{227}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$I, $^{125}$I, $^{131}$I, $^{189}$Ir, $^{191}$Ir, $^{192}$Ir, $^{194}$Ir, $^{52}$Fe, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Sr, $^{35}$S, $^{177}$Ta, $^{117m}$Sn, $^{121}$Sn, $^{166}$Yb, $^{169}$Yb, $^{90}$Y, $^{212}$Bi, $^{119}$Sb, $^{197}$Hg, $^{97}$Ru, $^{100}$Pd, $^{101m}$Rh, and $^{212}$Pb.

"Chemotherapeutic agent" as used herein includes but is not limited to methotrexate, daunomycin, mitomycin, cisplatin, vincristine, epirubicin, fluorouracil, verapamil, cyclophosphamide, cytosine arabinoside, aminopterin, bleomycin, mitomycin C, democolcine, etoposide, mithramycin, chlorambucil, melphalan, daunorubicin, doxorubicin, tamosifen, paclitaxel, vincristin, vinblastine, camptothecin, actinomycin D, and cytarabine "Cytotoxic agent" as used herein includes but is not limited to ricin (or more particularly the ricin A chain), aclacinomycin, diphtheria toxin. Monensin, Verrucarin A, Abrin, Vinca alkaloids, Tricothecenes, and Pseudomonas exotoxin A.

"Treat" as used herein refers to any type of treatment or prevention that imparts a benefit to a subject afflicted with a disease or at risk of developing the disease, including improvement in the condition of the subject (e.g., in one or more symptoms), delay in the progression of the disease, delay the onset of symptoms or slow the progression of symptoms, etc. As such, the term "treatment" also includes prophylactic treatment of the subject to prevent the onset of symptoms. As used herein, "treatment" and "prevention" are not necessarily meant to imply cure or complete abolition of symptoms." to any type of treatment that imparts a benefit to a patient afflicted with a disease, including improvement in the condition of the patient (e.g., in one or more symptoms), delay in the progression of the disease, etc.

"Treatment effective amount" as used herein means an amount of the antibody sufficient to produce a desirable effect upon a patient inflicted with lymphoma, including improvement in the condition of the patient (e.g., in one or more symptoms), delay in the progression of the disease, etc.

The present invention is primarily concerned with the treatment of human subjects, including male and female subjects and neonatal, infant, juvenile, adolescent, adult, and geriatric subjects, but the invention may also be carried out on animal subjects, particularly mammalian subjects such as mice, rats, dogs, cats, livestock and horses for veterinary purposes, and for drug screening and drug development purposes.

Native antibodies and immunoglobulins are usually heterotetrameric glycoproteins of about 150,000 daltons, composed of two identical light chains and two identical heavy chains. Each light chain is linked to a heavy chain by one covalent disulfide bond, while the number of disulfide linkages varies between the heavy chains of different immunoglobulin isotypes. Each heavy and light chain also has regularly spaced intra-chain disulfide bridges. Each heavy and light chain has at one end a variable domain followed by a number of constant domains; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Chothia et al. *J. Mol. Biol.* 186:651 (1985; Novotny and Haber, *Proc. Natl. Acad. Sci. U.S.A.* 82:4592 (1985); Chothia et al., *Nature* 342:877-883 (1989)).

The term "antibody" herein is used in the broadest sense and specifically covers monoclonal antibodies and polyclonal antibodies. Further, the term "antibody" as used herein includes antibody fragments which comprise a portion of a full length antibody and which retain the capability of binding to a target antigen, for example, Fab, Fab', F(ab')$_2$, and Fv fragments; diabodies; linear antibodies; single chain antibody molecules; and multispecific antibodies formed from antibody fragments. Such fragments are also produced by known techniques.

In addition, the term "antibody" refers to all types of immunoglobulins, including IgG, IgM, IgA, IgD, and IgE. The term "immunoglobulin" includes the subtypes of these immunoglobulins, such as IgG$_1$, IgG$_2$, IgG$_3$, IgG$_4$, etc. The antibodies may be of any species of origin, including (for example) mouse, rat, rabbit, horse, or human, or may be chimeric antibodies. See, e.g., M. Walker et al., *Molec. Immunol.* 26, 403-11 (1989). Such monoclonal antibodies are produced in accordance with known techniques.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to the specificity, the monoclonal antibodies are advantageous in that they are synthesized by the hybridoma cells, uncontaminated by other immunoglobulin producing cells. Alternatively, the monoclonal antibody may be produced by a cell stably or transiently transfected with the heavy and light chain genes encoding the monoclonal antibody.

The modifier "monoclonal" indicates that character of the antibody as being obtained from a substantially homogenous population of antibodies, and is not to be construed as requiring engineering og the antibody by any particular method. The term monoclonal is used herein to refer to an antibody that is derived from a clonal population of cells, including any eukaryotic, prokaryotic, or phage clone, and not the method by which the antibody was engineered. For example, the monoclonal antibodies to be used in accordance with the present invention may be the hybridoma method first described by Kohler et al., *Nature* 256:495 (1975), or may be made by any recombinant DNA method (see, e.g., U.S. Pat. No. 4,816,567) including isolation from phage antibody libraries using the techniques described in Clarkson et al., *Nature*, 352:624-628 (1991) and Marks et al., *J. Mol. Biol.*, 22:581-597 (1991), for example. These methods can be used to produce, for example, monoclonal mammalian, chimeric, humanized, human, and domain antibodies.

Monoclonal antibodies may be recombinant monoclonal antibodies produced according to the methods disclosed in Reading U.S. Pat. No. 4,474,893, or Cabilly et al., U.S. Pat. No. 4,816,567. The antibodies may also be chemically constructed by specific antibodies made according to the method disclosed in Segel et al., U.S. Pat. No. 4,676,980 (The disclosure of all U.S. patent references cited herein are intended to be incorporated herein by reference in their entirety).

Monoclonal antibodies may be chimeric or "humanized" antibodies produced in accordance with known techniques. For example, chimeric monoclonal antibodies may be complementarily determining region-grafted antibodies (or "CDR-grafted antibodies") produced in accordance with known techniques.

Monoclonal Fab fragments may be produced in *Escherichia coli* by recombinant techniques known to those skilled in the art. See, e.g., W. Huse, *Science* 246, 1275-81 (1989).

Antibodies for use in the present invention specifically bind to their target with a relatively high binding affinity, for example, with a dissociation constant of about $10^{-6}$ or $10^{-8}$ up to $10^{-12}$ or $10^{-13}$.

Humanized monoclonal antibodies are a further aspect of the present invention. A humanized antibody of the present invention may be produced from antibodies as described herein by any suitable technique, using a conventional complementarity determining region (CDR)-grafting method as disclosed in EPO Publication No. 0239400 and U.S. Pat. Nos. 6,407,213; 6,180,370; and 5,693,762, all of which are incorporated herein by reference in their entirety. Alternatively, a humanized antibody may be produced by directly modifying antibody variable regions without diminishing the native affinity of the domain for antigen while reducing its immunogenicity with respect to a heterologous species (see, e.g., U.S. Pat. No. 5,766,886 which is incorporated herein by reference in its entirety).

Using a CDR-grafting method, the humanized antibody is generally produced by combining a human framework region (FR) with one or more CDR's from a non-human (usually a mouse or rat) immunoglobulin which are capable of binding to a predetermined antigen.

Typically, the humanized antibody comprises substantially all of at least one, and typically two, variable domains (Fab, Fab', F(ab')$_2$, Fabc, Fv) in which all or substantially all of the CDR correspond to those of a non-human immunoglobulin and all or substantially all of the FR are those of a human immunoglobulin consensus sequence. The humanized antibody optimally also comprises at least a portion of an immunoglobulin constant region (Fc), typically that of a human immunoglobulin. Ordinarily, the antibody contains both the light chain as well as at least the variable domain of a heavy chain. The antibody also may include the CH1, hinge, CH2, CH3, and CH4 regions of the heavy chain.

The humanized antibody may be selected from any class of immunoglobulins, including IgM, IgG, IgD, IgA and IgE, and any isotype, including IgG$_1$, IgG$_2$, IgG$_3$ and IgG$_4$. Usually the constant domain is a complement fixing constant domain where it is desired that the humanized antibody exhibit cytotoxic activity, and the class is typically IgG$_1$. Where such cytotoxic activity is not desirable, the constant domain may be of the IgG$_2$ class. The humanized antibody may comprise sequences from more than one class or isotype, and selecting particular constant domains to optimize desired effector functions is within the ordinary skill in the art.

The term "variable" refers to the fact that certain portions of the variable domains differ extensively in sequence among antibodies and are responsible for the binding specificity of each particular antibody for its particular antigen. However, the variability is not evenly distributed through the variable domains of antibodies but rather is concentrated in three segments called "complementarity determining regions" (CDRs) (also called the "hypervariable regions") both in the light chain and the heavy chain variable domains. The CDR or hypervariable region comprises the amino acid residues of an antibody which are specifically responsible for binding to its antigen (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk. J. Mol. Biol. 196:901-917 (1987)).

The more highly conserved portions of the variable domains are called the framework regions (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody-dependent cell-mediated cytotoxicity (ADCC).

The antibody or polypeptide of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated.

In general, those skilled in the art will appreciate that minor deletions or substitutions may be made to the amino acid sequences of peptides of the present invention without unduly adversely affecting the activity thereof. Thus, peptides containing such deletions or substitutions are a further aspect of the present invention. In peptides containing substitutions or replacements of amino acids, one or more amino acids of a peptide sequence may be replaced by one or more other amino acids wherein such replacement does not affect the function of that sequence. Such changes can be guided by known similarities between amino acids in physical features such as charge density, hydro-phobicity/hydrophilicity, size and configuration, so that amino acids are substituted with other amino acids having essentially the same functional properties. For example: Ala may be replaced with Val or Ser; Val may be replaced with Ala, Leu, Met, or Ile, preferably Ala or Leu; Leu may be replaced with Ala, Val or Ile, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gln, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gln or Ser, preferably Ser; Lys may be replaced with Gln or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function by, for example, testing for the ability to bind to STRO-1.

In an embodiment of the present invention, a recombinant antibody comprises a heavy chain polypeptide having the sequence of SEQ ID NO:1, or any peptide fragment thereof, wherein the antibody binds to human STRO-1 cell surface protein. The peptide fragment of SEQ ID NO:1 may be any fragment of SEQ ID NO:1, or two or more fragments of SEQ ID NO:1, wherein the antibody binds to human STRO-1 cell surface protein.

In a further embodiment, the recombinant antibody comprises a heavy chain polypeptide further comprising a peptide fragment of SEQ ID NO:1 selected from the group of peptide fragments comprising the hypervariable regions of SEQ ID NO:1, amino acids 31-35 (GYYMH) (SEQ ID NO:3), 50-65 (RVNPNNGGTSYNQKFK) (SEQ ID NO:4) and 95-102 (YCATYAMD) (SEQ ID NO:5), or any combination thereof, wherein the antibody binds to human STRO-1 cell surface protein.

An additional embodiment of the present invention comprises a recombinant antibody comprising a heavy chain polypeptide further comprising the sequences SEQ ID NO:3, SEQ ID NO:4 and SEQ ID NO:5, wherein 14 amino acids separate SEQ ID NO:3 from SEQ ID NO:4, and 29 amino acids separate SEQ ID NO:4 from SEQ ID NO:5, and further wherein the antibody binds to human STRO-1 cell surface protein.

In another embodiment, the recombinant antibody further comprises a light chain polypeptide having the sequence of SEQ ID NO:2, or any peptide fragment thereof, wherein the antibody binds to human STRO-1 cell surface protein. The peptide fragment of the recombinant antibody may be any fragment of SEQ ID NO:2, or two or more fragments of SEQ ID NO:2, wherein the antibody binds to human STRO-1 cell surface protein.

In a further embodiment, the recombinant antibody of the present invention further comprises a light chain polypeptide comprising a peptide fragment of SEQ ID NO:2 selected from the group of peptide fragments comprising the hypervariable regions of SEQ ID NO:2, amino acids 24-34 (QTDYLTTSPGG) (SEQ ID NO:6), 50-56 (SNYANWV) (SEQ ID NO:7) and 89-97 (DKAALTITG) (SEQ ID NO:8), or any combination thereof, wherein the antibody binds to human STRO-1 cell surface protein.

In other embodiments of the present invention, a recombinant antibody comprises a light chain polypeptide comprising the sequences SEQ ID NO:6, SEQ ID NO:7 and SEQ ID NO:8, wherein 15 amino acids separate SEQ ID NO:6 from SEQ. ID NO:7, and 32 amino acids separate SEQ ID NO:7 from SEQ ID NO:8, and further wherein the antibody binds to human STRO-1 cell surface protein.

In a further embodiment, the antibody of the present invention is immobilized on a solid support. Methods of linking a wide variety of compounds, including biomolecules such as antibodies, to solid supports are well known in the art, and any suitable method can be used in connection with the present invention. Such methods are amply illustrated in the literature. See, for example, IMMOBILIZED ENZYMES, Ichiro Chibata, Halsted Press, New York, 1978, and Cuatrecasas, 1970, the disclosures of which are incorporated herein by reference. The capturing and control reagents may be covalently bound or non-covalently attached through nonspecific bonding. If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. In addition to covalent bonding, various methods for noncovalently binding an assay component can be used. Noncovalent binding is typically nonspecific absorption of a compound to the surface. Typically, the surface is blocked with a second compound to prevent non-specific binding of labeled assay components.

A variety of solid supports are known to the art, including organic and inorganic polymers, both natural and synthetic, which are suitable for use with the present invention. For instance, the solid support may be beads, membranes (e.g., nitrocellulose), microtiter wells (e.g., PVC or polystyrene), strings, plastic, strips, or any surface onto which antibodies may be deposited or immobilized. In addition, a wide variety of organic and inorganic polymers, both natural and synthetic, may be employed as the material for the solid surface. Illustrative polymers include polyethylene, polypropylene, poly(4-methylbutene), polystyrene, polymethacrylate, poly (ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that may be employed include paper, glasses, ceramics, metals, metalloids, semiconductive materials, cements or the like. In addition, substances that form gels, such as proteins (e.g., gelatins), lipopolysaccharides, silicates, agarose and polyacrylamides can be used. Polymers which form several aqueous phases, such as dextrans and polyalkylene glycols or surfactants, such as phospholipids or long chain (12-24 carbon atoms) alkyl ammonium salts and the like are also suitable. Where the solid surface is porous, various pore sizes can be employed depending upon the nature of the system.

In a further embodiment, the antibodies of the present invention are conjugated or otherwise linked or connected to detectable groups such as radiolabels (e.g., $^{35}$S, $^{125}$I, $^{32}$P, $^{13}$H, $^{14}$C, $^{131}$I), enzyme labels (e.g., horseradish peroxidase, alkaline phosphatase), gold beads, chemiluminescence labels, ligands (e.g., biotin) and/or fluorescence labels (e.g., fluorescein) in accordance with known techniques. Determination of the formation of an antibody/antigen complex in the methods of this invention can be by detection of, for example, precipitation, agglutination, flocculation, radioactivity, color development or change, fluorescence, luminescence, etc., as is well known in the art.

In an additional embodiment of the present invention, the antibodies of the present invention can be used to isolate and purify from a heterogeneous cell sample those cells that comprise the STRO-1 cell surface protein. Marrow cells that express STRO-1 antigen are capable of differentiating into multiple mesechymal lineages, including hematopoiesis-supportive stromal cells, adipocytes, osteoblasts, and chondrocytes. Thus, the antibodies of the present invention can be used to isolate highly concentrated compositions of cells that bind to the STRO-1 cell surface protein and that are substantially free of differentiated or dedicated cells.

For the purpose of isolating and purifying cells that express or comprise human STRO-1 cell surface protein, a cell sample is contacted with an antibody of the present invention under conditions whereby the antibody can bind to cells comprising the STRO-1 cell surface protein and cells in the cell sample binding to the antibody are isolated from the cells that do not bind to the antibody. Methods of isolation or separation of cells and biological molecules are well known in the art and include but are not limited to affinity chromatography and fluorescence activated cell sorting (FACS).

A further embodiment of the present invention is a method of detecting a cell in a cell sample, wherein the cell comprises the human STRO-1 cell surface protein, the method comprising contacting a cell sample with the antibody of the present invention under conditions whereby an antibody can bind the STRO-1 cell surface protein on the cell, and detecting the binding of the antibody to cells in the sample, thereby detecting the cells in the sample comprising human STRO-1 cell surface protein. For the purpose of detection, the antibody may be conjugated to detectable groups such as radiolabels (e.g., $^{35}S$, $^{125}I$, $^{32}P$, $^{13}H$, $^{14}C$, $^{131}I$), enzyme labels (e.g., horseradish peroxidase, alkaline phosphatase), gold beads, chemiluminescence labels, ligands (e.g., biotin) and/or fluorescence labels (e.g., fluorescein) in accordance with known techniques. Methods of detection of an antibody bound to STRO-1 on the surface of a cell include, but are not limited to, precipitation, agglutination, flocculation, radioactivity, color development or change, fluorescence, and luminescence.

The isolated cells of the present invention can be used for a variety of purposes including, but not limited to, cell based therapies and drug testing.

Inactivation of Stro-1 positive cells. Antibodies as described herein may be coupled to a therapeutic agent and administered to or contacted to Stro-1 positive stem cells to eliminate or inactivate (e.g., kill, stunt, or prevent from growing or replicating) Stro-1 positive cells. The method may be carried out in vitro or in vivo in accordance with known techniques.

Currently, adequate engraftment of stromal cells is not achieved when a stem cell transplant is performed. Without wishing to be bound to a particular theory for the present invention, this is believed to be due, at least in part, to the fact that resident stromal cells and their precursors are not ablated with pretransplant conditioning, so there is no "space" for donor stromal cells to engraft. In situations where stromal cell engraftment is desired, targeting the resident stromal cell may accordingly facilitate donor stroma engraftment.

In addition, removal or inactivation of resident stromal cells in vivo is desireable if they are functioning abnormally, either because of an intrinsic defect or viral induced changes.

Further, in vitro, such methods permit the dissection of the complex culture systems currently used to better mimic the marrow microenvironment.

Any therapeutic agent conventionally coupled to a monoclonal antibody may be employed, including (but not limited to) radionuclides, cytotoxic agents, and chemotherapeutic agents. See generally *Monoclonal Antibodies and Cancer Therapy* (R. Reisfeld and S. Sell Eds. 1985)(Alan R. Liss Inc. N.Y.). Therapeutic agents such as radionuclides, cytotoxic agents and chemotherapeutic agents are described above, and also described in U.S. Pat. Nos. 6,787,153; 6,783,760; 6,676,924; 6,455,026; and 6,274,118.

Therapeutic agents may be coupled to the antibody by direct means or indirect means (e.g., via a chelator) by any suitable technique, including but not limited to those described in U.S. Pat. Nos. 6,787,153; 6,783,760; 6,676,924; 6,455,026; and 6,274,118. Therapeutic agents may be coupled or conjugated to the antibody by the Iodogen method or with N-succinimidyl-3-(tri-n-butylstanyl)benzoate (the "ATE method"), as will be apparent to those skilled in the art. See, e.g., M. Zalutsky and A. Narula, *Appl. Radiat. Isot.* 38, 1051 (1987).

The therapeutic antibodies (those having a therapeutic agent coupled thereto) will generally be mixed, prior to in vivo administration, with a non-toxic, pharmaceutically acceptable carrier substance (e.g. normal saline or phosphate-buffered saline), and will be administered using any medically appropriate procedure, e.g., parenteral administration (e.g., injection) such as by intravenous or intra-arterial injection.

Therapeutic antibodies may be formulated for administration in a pharmaceutical carrier in accordance with known techniques. See, e.g., Remington, *The Science And Practice of Pharmacy* (9th Ed. 1995). In the manufacture of a pharmaceutical formulation according to the invention, the active compound (including the physiologically acceptable salts thereof) is typically admixed with, inter alia, an acceptable carrier. The carrier should be acceptable in the sense of being compatible with any other ingredients in the formulation and must not be deleterious to the patient. The carrier may be a liquid and is preferably formulated with the compound as a unit-dose formulation which may contain from 0.01 or 0.5% to 95% or 99% by weight of the active compound.

Dosage of the therapeutic antibody will likewise depend, among other things, the condition of the subject, the particular category or type of cancer being treated, the route of administration, the nature of the therapeutic agent employed, and the sensitivity of the tumor to the particular therapeutic agent. For example, the dosage will typically be about 1 to 10 micrograms per kilogram subject body weight. The specific dosage of the antibody is not critical, as long as it is effective to result in some beneficial effects in some individuals within an affected population. In general, the dosage may be as low as about 0.05, 0.1, 0.5, 1, 5, 10, 20 or 50 micrograms per kilogram subject body weight, or lower, and as high as about 5, 10, 20, 50, 75 or 100 micrograms per kilogram subject body weight, or even higher.

Additional discussion of uses for the Stro-1 antibodies described herein are provided in U.S. Pat. Nos. 7,122,178; 7,057,738; and 5,677,136; and in US Patent Application Publication Nos. 20060286077; 20060182724; 20060088890; and 20060057720.

The present invention is explained in greater detail in the following non-limiting Examples. The disclosures of all United States patent references cited herein are to be incorporated herein by reference.

EXAMPLE

STRO-1 Antibody Heavy and Light Chain Sequences

Two (2) mg of mouse IgM protein was submitted for variable region sequence analysis of both heavy and light chains. The sample was dissolved in PBS buffer to a final concentration of 1 mg/ml.

Reduction/alkylation and electrophoresis. The IgM protein was treated with 10 mM DTT at 65° C. for 60 min and then with 55 mM iodoacetylamide at 37° C. for 30 min in the dark. The treated sample was then loaded on SDS-page and Tricine gels. The heavy and light chains were separated, resulting in two bands at 90 kd and 25 kd, respectively.

Edman Degradation. The heavy chain and light chain were transferred from gel to PVDF membrane for Edman degradation.

Mass Spectrometry. The heavy chain and light chain bands were removed from acrylamide gels and digested separately with a single enzyme or a combination of proteolytic enzymes. The enzyme used are endoproteinase trypsin, endoproteinase Lys-C, endoproteinase AspN, and endoproteinase Glu-C. The resulting peptides are extracted and subject to MALDI-MSMS and ESI-MSMS for sequencing analysis. The sequencing data was used to search NCBl nr database, and the matched peptide sequences were checked manually for accuracy. De novo sequencing technique was also used for the good MSMS sequencing data, but with no good matches.

Results. The sequence of the Fv heavy chain is given in Table 1 below, and the sequence of the Fv light chain is given in Table 2 below.

TABLE 1

Fv sequences of heavy chain
(putative variable region: 1-114)

(SEQ ID NO: 1)
EVQLQQSGPD LVKPGASVKI SCKASGYSFT GYYMHWVKQS

HGKSLEWIGR VNPNNGGTSY NQKFKGKAIL TVDKSSSTAY

MELRSLTSED SAVYYCATYA MDYWGQGTSV TVSS

TABLE 2

Fv sequences of light chain
(putative variable region: 1-120)

(SEQ ID NO: 2)
WNDVLCSLVD LCRACSSQAS VSTQTDYLTT SPGGTVILTC

RCATGAVTTS NYANWVQEKP DHLFTGLIGG TSNRAPGVPV

RFSGSLIGDK AALTITGAQT EDDAMYFSSL WYYGGHGVFG

The foregoing is illustrative of the present invention, and is not to be construed as limiting thereof. The invention is defined by the following claims, with equivalents of the claims to be included therein.

That which is claimed is:

1. A recombinant antibody comprising a heavy chain polypeptide, wherein the heavy chain polypeptide comprises the amino acid sequence of SEQ ID NO:1(EVQLQQSGPD LVKPGASVKI SCKASGYSFT GYYMHWVKQS HGKSLEWIGR VNPNNGGTSY NQKFKGKAIL TVDKSSSTAY MELRSLTSED SAVYYCATYA MDYWGQGTSV TVSS, and further wherein said antibody binds to human STRO-1 cell surface protein.

2. The antibody according to claim 1, wherein the antibody is immobilized on a solid support.

3. The antibody according to claim 1, further comprising a detectable group conjugated thereto.

4. The recombinant antibody of claim 1, wherein the antibody further comprises a light chain polypeptide comprising the amino acid sequence of SEQ ID NO:2(WNDVLCSLVD LCRACSSQAS VSTQTDYLTT SPGGTVILTC RCATGAVTTS NYANWVQEKP DHLFTGLIGG TSNRAPGVPV RFSGSLIGDK AALTITGAQT EDDAMYFSSL WYYGGHGVFG), or hypervariable region thereof.

5. The recombinant antibody of claim 4, wherein the hypervariable region of SEQ ID NO:2 is selected from the group of sequences comprising SEQ ID NO:6(QTDYLTTSPGG), SEQ ID NO:7(SNYANWV) and SEQ ID NO:8 (DKAALTITG).

6. The antibody according to claim 4, wherein the antibody is immobilized on a solid support.

7. The antibody according to claim 4, further comprising a detectable group conjugated thereto.

8. A method of isolating a cell in a cell sample, wherein the cell binds an antibody to human STRO-1 cell surface protein, said method comprising:
   contacting the cell sample with an antibody so that the antibody binds the cell; and
   isolating the cell in the cell sample that binds to the antibody from the cells in the sample that do not bind to the antibody;
   wherein said antibody is a recombinant antibody comprising a heavy chain polypeptide, wherein said heavy chain polypeptide comprises .the amino acid sequence of SEQ ID NO:1(EVQLQQSGPD LVKPGASVKI SCKASGYSFT GYYMHWVKQS HGKSLEWIGR VNPNNGGTSY NQKFKGKAIL TVDKSSSTAY MELRSLTSED SAVYYCATYA MDYWGQGTSV TVSS).

9. The method of claim 8, wherein the antibody is immobilized in a solid support.

10. The method of claim 8, wherein the antibody further comprises a detectable group conjugated thereto.

11. A method of isolating a cell in a cell sample, wherein the cell binds an antibody to human STRO-1 cell surface protein, said method comprising:
    contacting the cell sample with an antibody so that the antibody binds the cell; and
    isolating the cell in the cell sample that binds to the antibody from the cells in the sample that do not bind to the antibody;
    wherein said antibody is a recombinant antibody comprising: (i) a heavy chain polypeptide, wherein the heavy chain polypeptide comprises the amino acid sequence of SEQ ID NO:1(EVQLQQSGPD LVKPGASVKI SCKASGYSFT GYYMHWVKQS HGKSLEWIGR VNPNNGGTSY NQKFKGKAIL TVDKSSSTAY MELRSLTSED SAVYYCATYA MDYWGQGTSV TVSS), and (ii) a light chain polypeptide comprising the amino acid sequence of SEQ ID NO:2(WNDVLCSLVD LCRACSSQAS VSTQTDYLTT SPGGTVILTC RCATGAVTTS NYANWVQEKP DHLFTGLIGG TSNRAPGVPV RFSGSLIGDK AALTITGAQT EDDAMYFSSL WYYGGHGVFG).

* * * * *